United States Patent [19]

Krauter et al.

[11] Patent Number: 4,714,075
[45] Date of Patent: Dec. 22, 1987

[54] BIOPSY CHANNEL FOR ENDOSCOPE

[75] Inventors: Allan I. Krauter, Syracuse; Robert L. Vivenzio, Auburn, both of N.Y.

[73] Assignee: Welch Allyn, Inc., Skaneateles Falls, N.Y.

[21] Appl. No.: 828,134

[22] Filed: Feb. 10, 1986

[51] Int. Cl.$^4$ ............................................. A61B 1/00
[52] U.S. Cl. ..................................................... 128/4
[58] Field of Search ........................................ 128/4-8; 73/151

[56] References Cited

U.S. PATENT DOCUMENTS

| 3,470,876 | 10/1969 | Barchilon | 128/4 |
| 3,670,721 | 6/1972 | Fukami et al. | 128/6 |
| 3,960,143 | 6/1976 | Terada | 128/4 |
| 3,998,216 | 12/1976 | Hosono | 128/6 |
| 4,245,624 | 1/1981 | Komiya | 128/4 |
| 4,327,711 | 5/1982 | Takagi | 128/4 |

FOREIGN PATENT DOCUMENTS 3242449  5/1983  Fed. Rep. of Germany .......... 128/4

Primary Examiner—William E. Kamm
Assistant Examiner—Max F. Hindenburg
Attorney, Agent, or Firm—Bruns and Wall

[57] ABSTRACT

A biopsy channel for use in the insertion tube of an endoscope or borescope having a reinforced length that passes through the steering section of the tube which can be bent to a small radius without collapsing or losing its circularity. The tubing is preferably a heat softenable thermoplastic and the reinforcement is a metal knitted fabric that is heat bonded into the outer surface of the tubing.

4 Claims, 4 Drawing Figures

BIOPSY CHANNEL FOR ENDOSCOPE

BACKGROUND OF THE INVENTION

This invention relates to an access channel for use in the insertion tube of an endoscope or a borescope through which a tool can be passed through the insertion tube into the viewing region of the instrument.

An endoscope or borescope is characterized by an elongated flexible insertion tube having a viewing head at its distal end and a control housing at its proximal end. A bendable steering unit is located at the distal end of the tube immediately behind the viewing head. One or two pairs of control cables pass through the insertion tube between steering knobs at the control housing and the steering unit. The cables can be selectively displaced to bend the steering section to either direct the viewing head at a desired target or to manipulate the viewing head through tight bends or turns. The steering unit is generally placed as close as possible to the viewing head so that it can be precisely turned in the smallest amount of space.

Endoscopes and borescopes are oftentimes equipped with an access channel that spans the length of the insertion tube between the control housing and the viewing head. The access channel is typically closed at the control housing by a penetratable seal and opens outwardly through the viewing head. Accordingly, a tool mounted upon the end of an elongated flexible rod can be passed through the channel into the viewing region of the instrument where it can be directed onto a given target to carry out a desired task. In the medical field, a biopsy tool is commonly passed through the channel to secure tissue samples from remote body cavities and hence this type of channel is commonly referred to as a "biopsy channel".

It is common practice to form a biopsy channel in two lengths or sections of tubing. A first relatively stiff section is mounted inside the insertion tube between the control housing and the steering unit. A second more flexible section is operatively coupled to the first section and arranged to pass through both the steering unit and the viewing head. Both sections of the channel exhibit good lubricity and thus offer little resistance to a tool as it moves therethrough. It has been found, however, that the more flexible front section of the tube which is situated inside the steering unit of the insertion tube is sometimes subjected to severe bending and torsional stresses that can kink and/or otherwise deform the channel to restrict or close the opening. When this occurs, a tool will be unable to transcend the bend region to complete the desired task.

SUMMARY OF THE INVENTION

It is therefore an object of the present invention to improve endoscopes and borescopes that are equipped with a tool access channel.

It is a further object of the present invention to provide an improved biopsy channel for use in an endoscope or a borescope that has a tubular section that is adapted to pass through the steering unit of the insertion tube which is flexible in bending and yet able to maintain a circular cross-sectional configuration when bent to a small radius.

Another object of the present invention is to reinforce a relatively thin-walled biopsy channel of an endoscope or borescope so that the channel will not close when it is bent to a tight radius.

Yet another object of the present invention is to provide an improved biopsy channel that is able to freely pass a tool therethrough when the channel is placed in a tight bend.

A still further object of the present invention is to provide a relatively inexpensive and easily fabricated lubricious biopsy channel having a reinforced section that has torsional stiffness and hoop strength for preventing the channel from closing when placed under torsional and/or bending stress.

These and other objects of the present invention are attained by a biopsy channel suitable for use in either an endoscope or a borescope that has a reinforced section that is situated within the steering unit of the instrument's insertion tube. The reinforced section of channel includes a tubular substrate formed of a heat softenable thermoplastic material having an open weave metal fabric heat bonded to its outer surface which furnishes both high torsionable and hoop strength to the reinforced section. The reinforced section is fabricated by placing the tubular substrate upon a mandrel and wrapping the outside of the substrate with an open mesh metal fabric. The tube and fabric assembly is drawn through a heated die that is maintained at a temperature high enough to soften the outer periphery of the tubular substrate. The metal fabric is forced inwardly into the softened material as it passes through the die cavity which, in turn, displaces substrate material outwardly through the mesh openings whereby the fabric is embedded in the outer surface of the reinforced section.

BRIEF DESCRIPTION OF THE DRAWINGS

For a better understanding of these and other objects of the present invention, reference is had to the following detailed description of the invention which is to be read in conjunction with the associated drawings, wherein.

DESCRIPTION OF THE INVENTION

Figure 1:
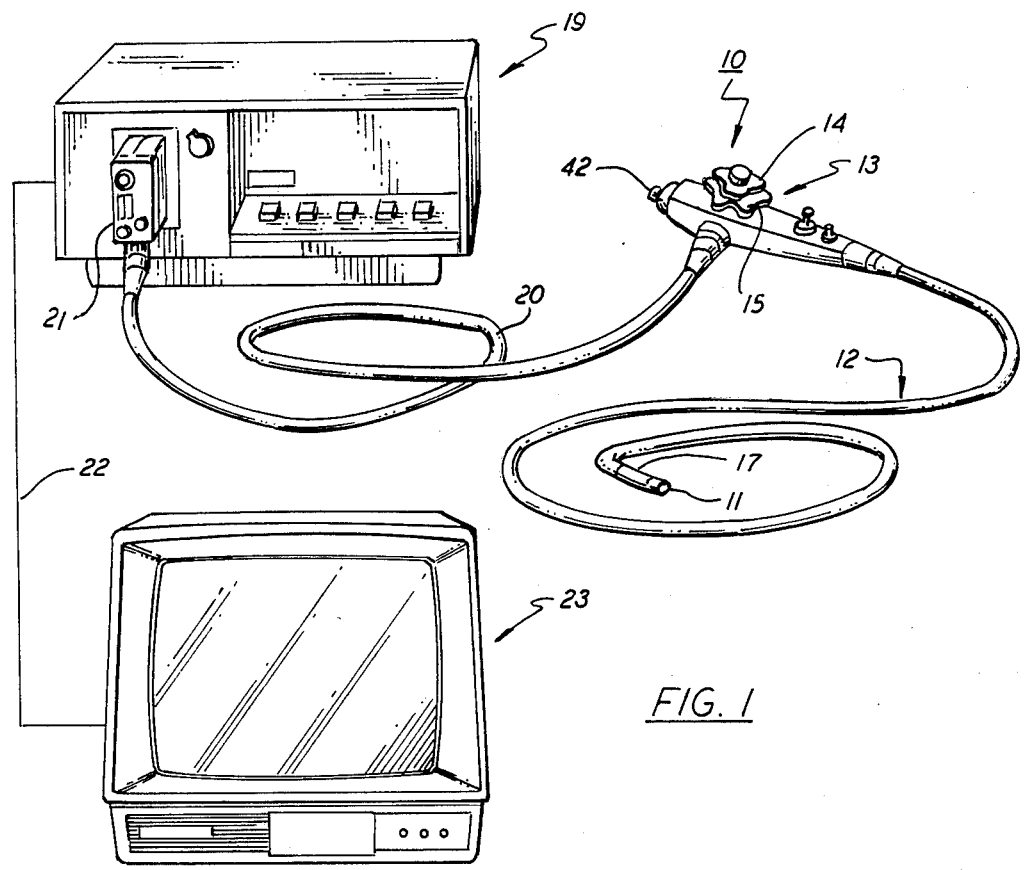
FIG. 1 is a perspective view of a video-equipped endoscopic instrument showing the component parts thereof.

Turning initially to FIG. 1, there is shown a video-equipped endoscope generally depicted at 10 of the type disclosed in U.S. Pat. No. Re. 3,1290, the disclosure of which is herein incorporated by reference to the extent necessary to understand the operation of the present instrument. An image sensor in the form of a charge coupled device (CCD) is mounted in the viewing head 11 located at the distal end of the insertion tube 12. The proximal end of the tube is operatively connected to a control housing 13 that contains a pair of control knobs 14 and 15 used to maneuver the distal end of the insertion tube. The knobs are connected to the steering unit 17 of the insertion tube by means of cables that extend through the tube. As explained in greater detail in co-pending application Ser. No. 806,667, filed Dec. 9, 1985, the steering unit is located immediately behind the viewing head.

The control housing is also connected to a video processor 19 by means of an umbilical cord 20 and a plug-in terminal 21. Video related signals are exchanged between the processor and the image sensor via electrical leads passing through the insertion tube and the umbilical cord. Video data provided to the processor by the sensor are placed in a suitable format for viewing and are transmitted by lead 22 to the video monitor 23 for viewing by the examining physician.

The insertion tube of an endoscope of the type illustrated in FIG. 1 is generally passed into a body cavity, such as the colon or stomach of a patient to visually inspect the tissue. Because the body passage leading to the inspection region is typically narrow and tortuous, the steering unit of the insertion tube must be able to bend as close to the viewing head as possible in order to precisely maneuver the head through the passage without causing harm to the patient. Once the head is situated in the desired target region, the steering unit is used to focus the optics of the viewing head upon the target so that a clear picture is presented to the physician.

Figure 2:
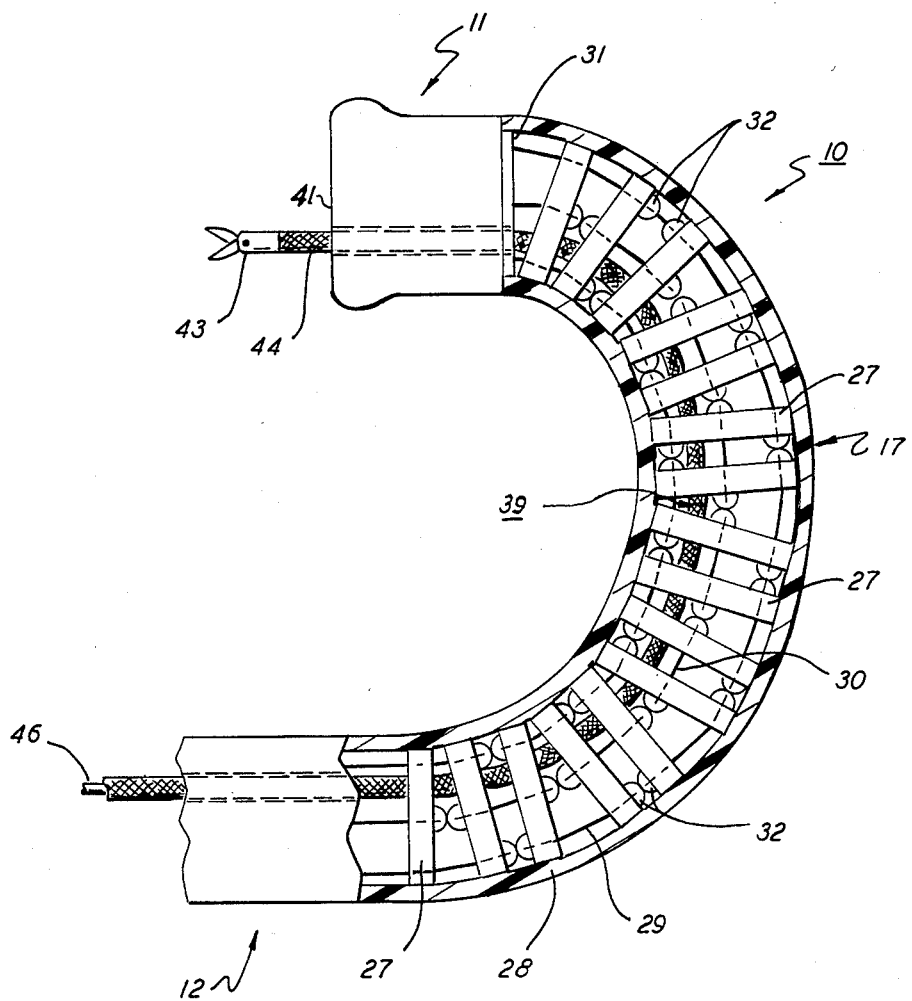
FIG. 2 is an enlarged view of the distal end of the insertion tube used in the endoscope of FIG. 1 showing the steering unit placed in a small radius bend.

As shown in FIG. 2, the distal end of the insertion tube 12 includes the noted viewing head 11 that is secured to the steering unit 17. The steering unit is formed by a series of flat washers 27—27 that are stacked in a face-to-face relationship within the flexible sheath 28 of the insertion tube. Two pairs of steering cables, depicted as 29 and 30, are passed through suitable openings in the washers. Each cable is anchored at one end in the back of the viewing head and is attached to a suitable mechanism connected to the control knobs so that each cable has two opposed runs passing through the stack. Hemispherical-shaped beads 32—32 are disposed over the cables within the spaces separating the washers. The flat face of each bead rests against the end face of a washer while the spherical face of the bead rides in rolling contact with the spherical face of a companion bead to form a hinge set. Two hinge sets are positioned in the space separating the adjacent washers with the two sets being mounted on the opposed runs of the same cable. The hinge sets are mounted on opposite cables in alternate spaces so that the steering unit can be bent in two distinct lanes that are generally 90 degrees apart. As can be seen by manipulating the control knobs, the viewing head can be precisely turned about 180 degrees in a very tight radius.

As noted, the stacked washers in the steering unit are covered with flexible sheath 28 that forms the outer liner of the insertion tube. Each washer contains a central passage that allows various system-related components to freely pass through the steering section. These may include a light transmitting fiber bundle, video-related leads to and from the image sensor assembly and a biopsy channel for providing tool access to a target in the viewing region of the head. For the sake of clarity only, the biopsy channel 39 is shown in FIG. 2. The biopsy channel extends the full length of the insertion tube and opens into the target region through the front face 41 of the viewing head. The proximal end of the channel extends into the control housing and is coupled to a luer lock connecter (not shown) which, in turn, is closed by a penetratable seal 42 (FIG. 1) at the back of the housing. A biopsy forcep 43, which is mounted upon the distal end of a flexible probe 44, is shown in FIG. 2 extended through the viewing head into the target region where it can take a tissue sample. The probe 44 is a hollow wound wire cable having an actuator wire 46 passing axially along its length for opening and closing the forceps. Although a biopsy forcep is shown in the present embodiment of the invention, it should be understood that any suitable tool as shown and used in the art can be used in the present invention.

Because the biopsy channel passes through the steering unit of the insertion tube, it will at certain times be subjected to severe bending and/or twisting as the head is being manipulated to maneuver or position the viewing head. These actions, alone or in combination, can restrict or even close the channel opening and thus prevent passage of a tool through this critical region. As will be explained below, the present biopsy channel is reinforced at least along the length of tubing that passes through the steering unit so that it resists both bending and torsional stress that might normally collapse or close off the biopsy channel opening.

Figure 3:
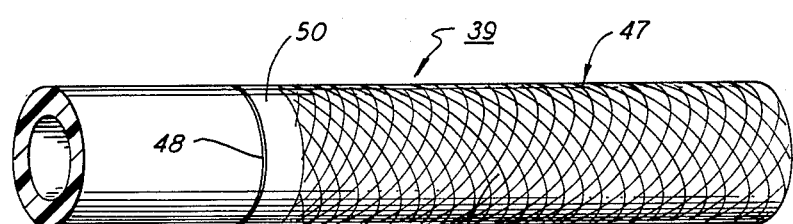
FIG. 3 is a further enlarged perspective view in section showing a length of biopsy channel embodying the teachings of the present invention.

FIG. 3 is a partial view of a biopsy channel 39 embodying the present invention. The channel includes a front tubular section 47 that is bonded at seam 48 by any suitable means to a complementary rear tubular section 49. The front section 47, in assembly, is situated inside the steering section and viewing head of the insertion tube and therefore exposed to higher stressing than the remainder of the channel. The front section is formed of a flexible thermoplastic tubular substrate 50, that is preferably a heat softenable vinyl material. A knitted or braided fabric 51 of open mesh construction encircles the front section of the channel and is thermally bonded to the tubing so that the fiber strands are at least partially and preferably fully embedded beneath the outer periphery of the tubing. The rear section 49 of the channel is formed from a single piece of stiffer plastic tubing, preferably Teflon, which passes back through the insertion tube into the control housing. The Teflon and vinyl tube sections coact to provide a highly lubricious channel through which a tool, such as a biopsy forceps, will freely slide as it is moved into or out of the target region of the instrument.

Figure 4:
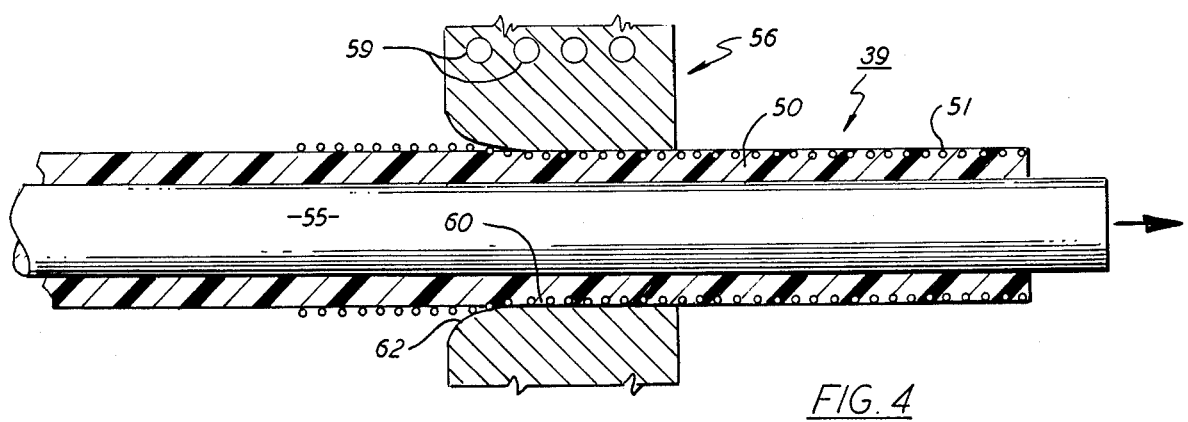
FIG. 4 is a side elevation in section showing a reinforced length of channel in the process of being manufactured by drawing the tubing through a heated die.

Turning now to FIG. 4 there is shown an extrusion die 56 used in the fabrication of the reinforced front section 47 of the channel. Initially, the heat softenable thermoplastic substrate 50 is passed over a cylindrical mandrel 55. A close running fit is provided between the inside diameter of the tubing and the outside diameter of the mandrel so that the tubing is snugly seated on the mandrel. A knitted wire fabric similar to that used for shielding electrical cable is slipped over the tubing. The fabric is preferably cylindrical in form and contains an open weave which is used in many well known braids or weaves conventionally used in the art. One such fabric is described in U.S. Pat. No. 4,375,009. The fabric strands are woven so that the cylinder can be stretched axially while correspondingly reduced in diameter to accommodate for differences in tube sizes.

The mandrel, the tubing and the knitted fabric are drawn, as an assembly, through a heated die 56 having a circular opening 60 formed therein. A series of internal electrical heating elements 59—59 are disposed throughout the die for raising the temperature at the die opening to a level sufficient to soften the outer portion of the tube passing therethrough. The heating elements are connected by leads to a suitable supply of electrical energy (not shown). The diameter of the die opening 60 is set for the desired outside diameter of the biopsy channel which, in practice, is slightly less than the outside diameter of the thermoplastic tubing.

The entrance to the die opening has an expanded mouth 62 that guides the tubing and the reinforcing fabric into the opening. As the tubing is drawn into the die opening, the outer surface of the tubing is thermally softened so that the reinforcing fabric is forced inwardly into the softened material. At the same time, the displaced substrate material is forced outwardly through the mesh openings between the fabric strands thereby filling the mesh openings and embedding the wire in the tube. The reinforcing fabric and the tubing are both compressed slightly by the die into a composite structure with the fabric being either partially or completely embedded in the tube. Preferably, the fabric is embedded below the surface of the thermoplastic so that a low friction lubricious surface is presented to objects inside the insertion tube that it might come in contact with.

Upon removal from the mandrel, the reinforced section is joined to the stiffer rear section of the biopsy channel to complete the biopsy channel. The reinforced section is mounted within the insertion tube as shown in FIG. 2 so that it is situated inside the steering unit. The knitted wire fabric, because of its ability to stretch axially, permits the biopsy channel to follow the insertion tube through a small radius bend without collapsing or otherwise losing its circular configuration in the critical bend region. The fabric furthermore supports the reinforced section to prevent the tube from being torsionally deformed under stress.

Although the present invention has been described with reference to a two piece biopsy channel, it should be understood that the invention is not limited to a specific configuration. For example, the channel can be constructed from a single piece of heat softenable tubing having reinforcing fabric embedded only within that section that transcends the steering unit. In certain cases, it may be important to extend the fabric along the entire length of the channel. In any event, the biopsy channel of the invention will contain an open mesh fabric embedded in the tubular substrate in regions that are subjected to severe bending to insure that the channel opening will not collapse during bending thus rendering the channel unusable for its intended purpose.

While this invention has been described in detail with respect to a preferred embodiment, it should be understood that this invention is not limited to that embodiment, and that many modifications and variations thereof could be effected by those skilled in the art without departure from the scope and spirit of this invention, as defined in the appended claims.

I claim:

1. An endoscope including an insertion tube that is connected at its proximal end to a control housing and having a bendable steering unit for maneuvering a viewing head located at the distal end of the tube, the steering unit being located near the distal end of the insertion tube adjacent the viewing head, said endoscope further including a lubricious biopsy channel passing through the inside of the insertion tube having a first tubular section contained within the steering unit that is joined to a second tubular section that passes back into the control housing, said first section being formed of a bendable heat softenable thermoplastic material that is encircled by open mesh metal fabric, said second section being formed of a stiffer plastic material that has a greater resistance to bending than the first section, and the open mesh metal fabric having fibers that are at least partially embedded in the outer surface of the first section for reinforcing said section to prevent the section from closing when bent to a small radius.

2. The endoscope of claim 1 wherein said first section is formed of vinyl and the second section is formed of Teflon.

3. Th endoscope of claim 1 wherein the metal fabric is woven into a cylinder that substantially encloses the first section of the biopsy channel.

4. The endoscope of claim 1 wherein the strands of the metal fabric are completely embedded beneath the outer surface of the first section.

* * * * *